United States Patent [19]

Shapiro

[11] Patent Number: 5,443,476
[45] Date of Patent: Aug. 22, 1995

[54] MICROSURGICAL SCISSOR APPARATUS WITH ROTARY CUTTING BLADE

[76] Inventor: Henry Shapiro, 328 Downham Ct., Walnut Creek, Calif. 94598

[21] Appl. No.: 151,354

[22] Filed: Nov. 12, 1993

[51] Int. Cl.⁶ .............................................. A61B 17/32
[52] U.S. Cl. ..................................... 606/174; 606/170
[58] Field of Search ........ 606/167, 170, 174, 205–210; 128/750–755

[56] References Cited

U.S. PATENT DOCUMENTS

| | | |
|---|---|---|
| 984,756 | 2/1911 | Frisch . |
| 2,137,710 | 11/1938 | Anderson . |
| 2,708,437 | 5/1955 | Hutchins . |
| 2,790,437 | 4/1959 | Moore . |
| 2,894,324 | 6/1959 | Hardin . |
| 3,995,619 | 12/1976 | Glatzer . |
| 4,258,716 | 3/1981 | Sutherland . |
| 4,433,687 | 2/1984 | Burke et al. ................ 606/174 |
| 4,499,899 | 2/1985 | Lyons, III ................. 606/174 |
| 4,590,936 | 5/1986 | Straub et al. .............. 606/174 |
| 5,370,658 | 12/1994 | Scheller et al. ........... 606/174 |

FOREIGN PATENT DOCUMENTS 8401281  4/1984  WIPO ................... 606/174

Primary Examiner—Stephen C. Pellegrino
Assistant Examiner—William Lewis
Attorney, Agent, or Firm—George W. Wasson

[57] ABSTRACT

A microsurgical instrument providing scissor action cutting elements at the end of an elongated tubular housing. One of the cutting elements is rotated with respect to the other in a plane transverse to the axis of the tubular housing. The cutting elements are at the free end of a tubular housing that is adapted to be inserted into a surgery site and has one end attached to a motion producing portion of the instrument that is outside the surgery site. The cutting elements are located at the end of the elongated tubular housing and are transverse to the axis of the housing. A stationary cutting blade is fixed to the housing and a rotatable cutting blade having a shaft is supported within the tubular housing. The motion producing portion of the instrument is hand-holdable and includes mechanical elements for converting reciprocal motion into rotary motion for operation of the rotatable cutting blade.

8 Claims, 2 Drawing Sheets

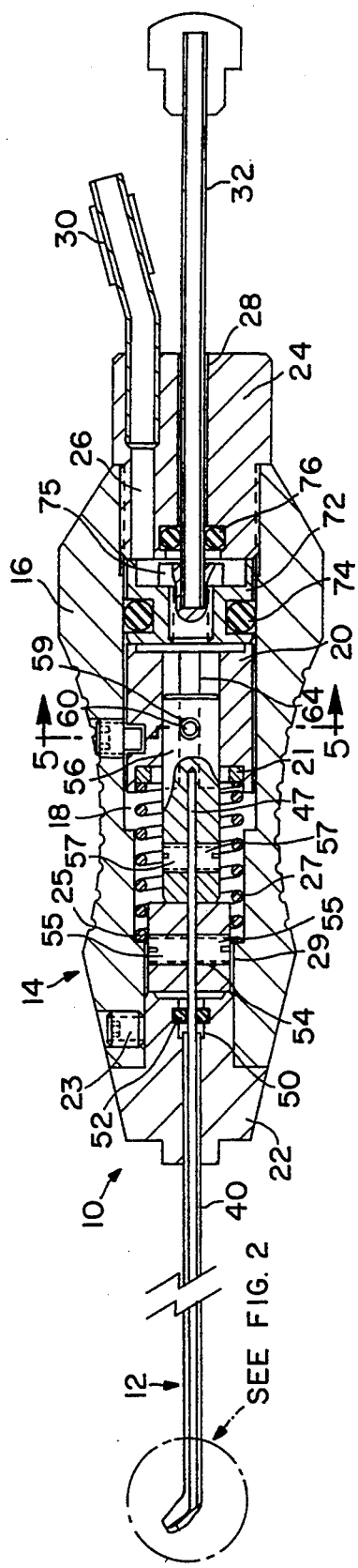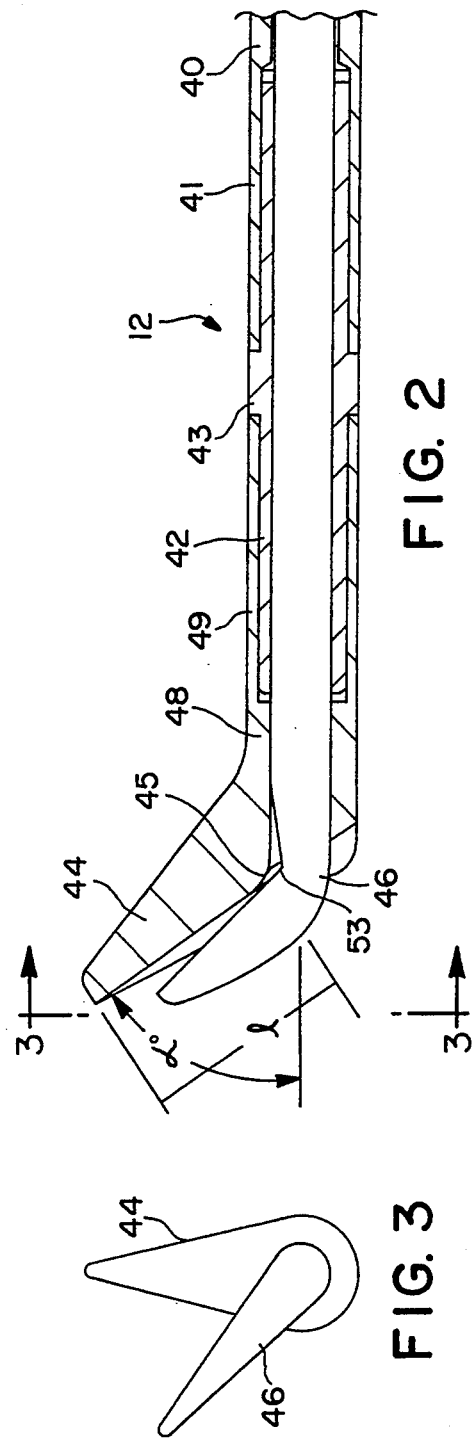

MICROSURGICAL SCISSOR APPARATUS WITH ROTARY CUTTING BLADE

This invention relates generally to a surgical instrument and more particularly to microsurgical instrument having scissor action cutting surfaces acting at the end of an elongated tubular housing that is adapted to be inserted into the region where surgery is to be performed. The scissor action cutting surfaces of the present invention accomplish their cutting action by moving one surface with respect to the other in a rotary action in a plane that is at a transverse angle with respect to the axis of the surgical instrument. One use of the apparatus of the present invention is in performing opthalmic surgery.

BACKGROUND OF THE INVENTION

The use of an elongated tubular instrument for insertion into a surgical site is known and such instruments have been used in performing microsurgical operations within eyes and other internal portions of a patient. In such microsurgical operations it is frequently necessary to cut materials within the surgery site and the need for very small scissor action surgical instruments for performing such cutting have been needed. Scissor action cutting elements of such surgical instruments may include cutting blades that are moved with respect to each other along the axis of the instrument (sometimes known in the art as vertical scissors) or transverse to the axis of the instrument (sometimes known in the art as horizontal scissors). One such scissor action apparatus having cutting blades that are moved with respect to each other along the axis of the instrument is shown in my copending application Ser. No. 953,075, filed Nov. 2, 1992 for MICROSURGICAL SCISSOR APPARATUS and other patents cited in that application. U.S. Pat. No. 4,258,716, issued Mar. 31, 1981 to Geoffrey Sutherland for MICROSURGICAL INSTRUMENTS discloses a scissor action cutting apparatus having cutting blades that are moved with respect to each other along a plane that is transverse to the axis of the instrument.

The elongated tubular members of microsurgical instruments that are inserted into the surgical site are used to transfer motion from motion producing elements outside of the surgical site to elements that are within the surgical site. It becomes necessary for successful useage of the instruments that the moving elements at the end of the elongated tubular member within the surgical site accomplish their movements in a smooth and controlled manner and with a minimum of undesirable or uncontrolled movements. Accomplishing the control of the moving elements and the reduction of motion resistance through the elongated tubular member has been the objective of many developments in the microsurgical instruments.

In scissor action cutting elements functioning at the end of an elongated tubular member where two cutting surfaces are moved with respect to each other it becomes desirable to cause the scissor cutting surfaces to move in a smooth motion and at a substantially uniform cooperating engagement throughout the entire scissor action. Accomplishing those desires at the free end of an elongated tubular microsurgery element becomes difficult.

Accordingly, one object of the present invention is the provision of a microsurgical apparatus having scissor action cutting elements at the free end of an elongated tubular member adapted to be inserted into a surgery site with motion elements outside of the surgery site for transferring motion through the tubular member to cause the scissor action at the cutting elements within the surgery site.

A further object of the present invention in accord with the preceeding object is an assembly of elements and members in a microsurgical instrument that will permit smooth rotated cutting motion at the scissor action cutting elements within a surgical site.

Another object of the present invention in accord with the preceeding objects is a construction and assembly of elements that will cause the rotary scissor action operating element at the free end of a tubular element to be firmly pressed against the stationary element.

Another object of the present invention in accord with the preceeding objects is to provide a construction of elements for the scissor elements and the operating mechanisms that can be easily assembled, aligned and adjusted to insure the proper cooperation on the cutting blades of the scissor action cutting surfaces throughout the entire moving cooperation of the blades.

A further object of the present invention in accord with the preceeding objects is to provide an assembly of elements that may be comfortably and conveniently held by a user and easily operated either manually or powered.

A further object of the present invention in accord with the preceeding objects is a mechanism for converting reciprocal motion to rotary motion for rotary operation of a movable blade with respect to a stationary blade in a microsurgical apparatus.

These and other objects and features of the present invention will be readily apparent to those skilled in the art from the appended drawings and specification illustrating a preferred embodiment wherein:

BRIEF DESCRIPTION OF THE DRAWINGS

FIG. 1 is a cross-sectional assembly view of the surgical instrument of the present invention showing the hand held motion producing portion and the elongated tubular portion of the instrument.

FIG. 2 is an enlarged partial sectional view of the circled portion A of FIG. 1 showing the scissor elements in their cooperating position.

FIG. 3 is an elevational view of taken along the lines 3—3 of FIG. 2.

DESCRIPTION OF THE PREFERRED EMBODIMENT

Figure 4:
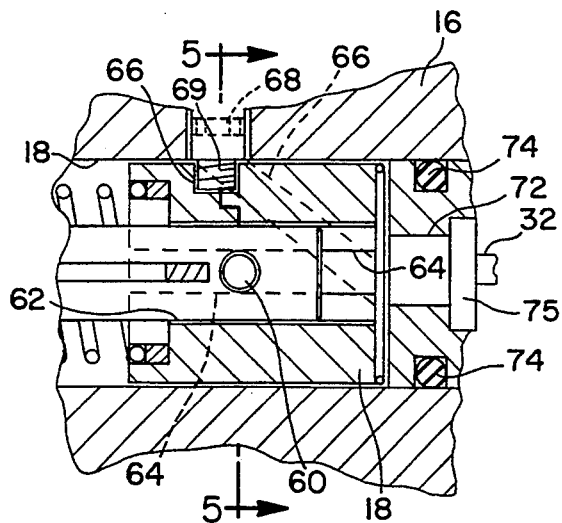
FIG. 4 is an enlarged partial sectional view of the means shown in FIG. 1 for converting reciprocable movement to rotary movement.

Referring to FIG. 1 of the drawings in detail, reference numeral 10 designates the assembled surgical instrument of the present invention with its cutting end in the form of a scissor action cutting attachment comprising an elongated tubular housing 12 and a stationary or hand held portion 14. The elongated tubular housing 12 has one end attached to the stationary portion 14 and a free end that is intended to be positioned within the surgery site. Within the stationary hand held portion 14 the motion is developed for moving the cutting blade portions in the desired directions within and outside the free end of the tubular housing 12. The stationary or hand held driving end includes connections for actuating the motion producing elements and for adjusting and positioning elements within the assembled surgical instrument.

The stationary or hand held driving end 14 could have many differing forms, the form shown here is a preferred embodiment that produces the desired relative motion within the cutting end 12. The exterior of driving end 14 is preferably cylindrical and contoured to be easily and hand held in a pencil-like grip and includes a body portion 16 having an internal cylindrical cavity 18 for cooperation with a piston 20. One end of the body portion 16 is closed by a needle holder 22 held in the body portion 16 by set screw 23. The needle holder has a central hold through which the elongated tubular housing or needle portion 12 of the instrument passes. The other end of the body portion 16 is internally threaded to receive a threaded end of a cover 24. The cover 24 includes passageways 26 and 28 for an air (or other operating medium) tube 30 and a manually operatable element 32, respectively.

The cylindrical cavity 18 has extending coaxial cavities toward the needle holder 22 including a reduced diameter portion with a shoulder 25 to accommodate a spring element 27 operating between the shoulder 25 and an end of the piston 20 within the cavity 18, and a further reduced diameter portion 29 providing entry access for the assembled elements of the tubular housing portion 12, to be described. At the cover 24 end the cylindrical cavity 18 is threaded to engage the threads of the cover 24.

Referring now to the mounting, alignment and adjustment portions for the tubular housing portion 12 and the assembly of the fixed and movable scissor action cutting blades of the attachment as shown in FIGS. 1 and 2, the tubular housing portion 12 includes a tubular element 40 adapted to be attached to the needle holder 22 as will be later described, an extending bushing portion 42 and a stationary blade 44, all of those elements being hollow and adapted to internally accommodate the rotatable shaft portion 47 of the movable blade 46. The bushing 42 has an external collar 43 that has an external diameter at least about the diameter of the tubular portion 40 and the body 48 of the stationary blade 44. Both the tubular housing 40 and the body portion 48 have internally enlarged diameter portions at 41 and 49, respectively, that are adapted to cooperate with and become attached to the exterior of the bushing 42 in alignment with the external collar 43 to provide an assembly at the cutting end of the tubular housing. The cooperating surfaces at the interior of the stationary blade body portion at 49 and the exterior of the bushing 42 as well as the interior of the tubular housing at 41 and the exterior of the bushing 42 are joined by suitable means such as bonding, welding or other suitable means to establish a substantially solid assembly into which the shaft 47 of the movable rotary blade 46 may be inserted. The purpose of this assembly is to provide firm cooperation between the body portion 48 of the stationary blade 44 and the tubular housing 40 while providing a firm and free rotary support for rotary movement of the shaft 47 of the movable blade 46 within the tubular housing portion 12 at the surgery site.

The stationary and movable blades are then assembled for insertion into the hand held portion 16; this assembly being done before the assembly is inserted into the hand held portion. With the movable blade 46 positioned within the bushing 42 as illustrated in FIG. 2, the tubular housing 40 is inserted within the axial hole through the needle holder 22 and an end of the housing 40 is flared, as shown in FIG. 1, to become firmly attached to the interior surface of the needle holder at 50 and an O-ring 52 is fitted around the extending portion of the movable blade shaft 47 and into an internal groove in the axial hole through the holder so as to seal the internal end of the needle holder 22.

The movable blade shaft 47 is then axially moved within the needle holder 22 to position the base 53 of the movable blade with the base 45 of the stationary blade 44 in the desired position for proper cutting action between the cutting surfaces of the blades. This axial alignment is done with the cutting blades in their open position as shown in FIG. 3. When so aligned axially, an axial holder 54 is attached to shaft 47 of the movable blade with the holder 54 engaging the inner end of the needle holder 22 and then a pair of set screws 55 are tightened against the shaft to fix the axial alignment of the blades.

The movable blade shaft 47 is then rotated to align the movable cutting blade 46 with the stationary cutting blade 44 as shown in FIG. 3 in any desired angular relationship of the blades and, when so aligned rotationally, a spindle 56 having an axial hole is positioned around the movable blade shaft 47 and fixed in position by a pair of threaded set screws 57 with an inner surface contacting a surface of the holder 54 and an exterior surface extending into the internal cylindrical cavity 18. Near the end of the spindle 56 at the portion within the cavity 18 a transverse hold 59 is drilled through the spindle and a pin 60 passes through the hole for cooperation with a groove in an element to be described.

The assembly of the blades and the tubular housing portion 12 is then in condition for insertion into the hand held portion 14 and the needle holder 22 prepared for attachment to the body portion 16 by tightening set screw 23 through the body portion and onto the interior extension of the needle holder 22. The needle holder 22 may have to be hole 62 adapted to fit snuggly around the spindle 56 while permitting axial movement between the piston 20 and the spindle 56.

hole 62 adapted to fit snuggly around the spindle 56 while permitting axial movement between the piston 20 and the spindle 56.

Figure 5:
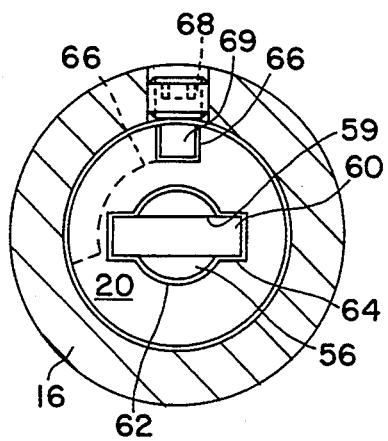
FIG. 5 is a sectional view taken along the lines 5—5 of FIG. 1 or FIG. 4.

The piston 20 has an internal groove and an external groove cut into its surfaces as is more easily seen in FIGS. 4 and 5. The internal groove is a pair of radial grooves 64 extending outwardly and only partially through the interior of the piston 20. The internal grooves 64 are adapted to accomodate pin 60 extending through hole 59 in spindle 56. The grooves 64 would permit piston 20 to move axially without moving spindle 56 if there were no other control over the movement of the piston 20. The external groove is a spiral groove 66 extending around the circumference of the piston from a position near the end of the piston nearest to the the spring 18 to a position near the end of the piston nearest to the end cap 24. A set screw 68 with an extension 69 is threaded through a hole in the body portion 16 with the extension 69 extending into the spiral groove 66. The extension 69 and the spiral groove 66 are in a cooperating alignment so that axial movement of the piston initiates rotary movement of the piston as the extension 69 forces the piston to rotate to keep the extension within the spiral groove 66. Rotary movement of the piston 20 is translated to rotary movement but not axial movement of the spindle 56 as the pin 60 slides within the radial grooves 64.

It should be noted that a portion of the external groove 66 will have to be aligned with the extension 69 of the set screw 68 to complete the assembly and that the needle holder 22 set screw 23 may have to be loosened to rotate the internal assembly or the piston 20 may have to be moved axially to establish the desried groove and extension alignment.

The remainder of the operating mechanism of the microsurgical scissor apparatus includes a piston operator 72 adapted for reciprocatable operation within the cavity 18 either under manual operation or driven operation. An O-ring 74 positioned within a groove in the piston operator 72 seals the piston operator 72 to the interior of the cavity 18. A pressure connection is made to the cover 24 through passageway 26 for driven operation of the piston operator 72. The manual operator 32 is attached by a threaded connector 75 to the piston operator 72 and an O-ring 76 seals the operator 32 from the cavity 18 and the powered operation of the piston operator 72. With the cover 24 securely fastened to the body portion 16, the operating mechanisms of the apparatus are complete. Either manual or powered operation of the piston operator 72 causes the piston 20 to be moved toward the needle holder 22 to produce rotary motion of the movable blade 46 with respect to the stationary blade 44. On completion of the desired cutting action or release of the manual or powered operation, the spring 27 biases the piston 20 back away from the needle holder end to place the cutter blades in open position as the set screw extension 69 moves along the groove 66 to rotate the movable blade to open position. The manual operation is also used in the insertion of the needle holder or tubular member into the surgery site when the scissor blades should be closed to permit easy of entry in to the site.

Figure 6:
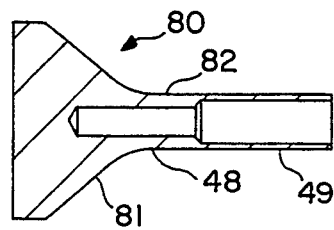
FIG. 6 is a sectional view of a blank element from which the stationary blade of the present invention may be formed.
Figure 7:
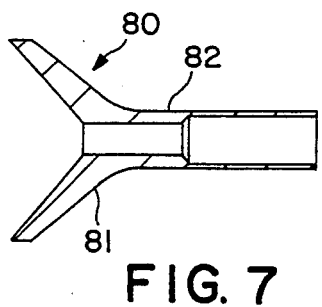
FIG. 7 is a first stage of machining the blank of FIG. 6 to form the stationary blade.
Figure 8:
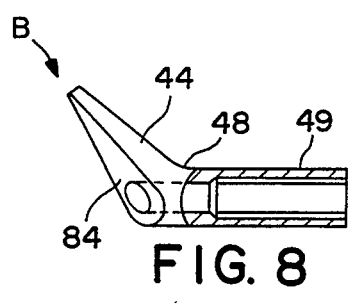
FIG. 8 is a second stage or machining the first stage element of FIG. 7 to form the finished stationary blade.
Figure 9:
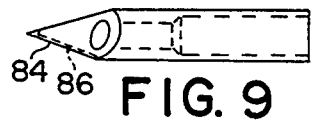
FIG. 9 is a rotated view of FIG. 8 showing the finished stationary blade.
Figure 10:
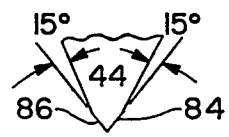
FIG. 10 is an end view of a finished blade taken along the line of arrow B of FIG. 8 and showing the angles of the cutting surfaces of the stationary blade.

FIGS. 6 to 10 relate to the formation of the stationary blade 44 from a blank element 80 in the form shown in FIG. 6. The blank element 80 has a cylindrical cone-like portion 81 with a stem portion 82. The stem portion is initially drilled to produce the body portion 48 and the enlarged diameter portion 49. The blank 80 is then machined to remove the interior of the cone-like portion 81, as shown in FIG. 7, and to produce a connection between the internal drilled hole. Most of the remaining cone-like portion 81 is then removed, as shown in FIG. 8 and 9, to leave only the stationary blade portion 44 and the interior face of the remaining cone-like portion is machined at a transverse angle to the axis of the hole through the blade to produce a first cutting edge 84. The opposite side of the cutting edge 84 is then machined at another transverse angle to produce a second cutting edge 86 as seen in FIG. 10. The formation of the stationary cutting blade as described permits the blade to be formed from hard sharpenable materials that can then be fastened to the bushing 42 which may have superior rotary support characteristics and the tubular element 40 which may have reasonably flexible characteristics.

The movable blade 46 may be similarly formed from hard sharpenable materials with its cutting surfaces formed to cooperate with the cutting surfaces 84 and 86 of the stationary blade 44 with the movable blade 46 being flexible enough to have a true scissor action cutting engagement with the stationary blade while the tip of the movable blade flexes away from the axis of the apparatus as the blades engage in their scissor action with rotation of the movable blade.

In FIGS. 2, 3 and 10 lengths and angles are shown for the transverse planes of the cutting blades with respect to the axis of the surgical instrument. It should be understood that the angle can be any desired angle between substantially 0° to 90° and the length of the stationary cutting blade may be limited only by the ability of the instrument to be inserted into a surgery site. Further, the rotational angle for the movement of the movable blade with respect to the stationary blade, as shown in FIG. 3, can be adjusted by the initial alignment of the blades in a rotary sense by connection of the rotary blade shaft 47 to the spindle 56 and the circumferential distance of the spiral groove 66 around the piston 20. Further, the speed of rotary movement of the movable blade can be varied by the cut of the path that the spiral groove 66 taxes so that initial cutting may be slow or fast dependent upon the slope of the path of the groove.

The construction of the microsurgical scissor apparatus of the present invention permits the elements to be formed and machined in a reasonably easy sense and then assembled into the completed apparatus with relative ease. It should be understood that the apparatus is extremely small in the cutting areas where typical dimensions of the diameter of the tubular holder 40 could be 0.036 inches, the diameter of the movable blade shaft could be 0.020 inches, the length of the stationary cutting blade could be between 0.067 inches and 0.122 inches, the overall length of the assembled apparatus could be 4.22 inches, the length of the assembled stationary blade and movable blade from tip to the outside edge of the needle holder could be 1.22 inches, and the length of the body portion from the needle holder 22 to the cover 24 could be 1.805 inches.

While certain preferred embodiments of the invention have been specifically disclosed, it should be understood that the invention is not limited thereto as many variations will be readily apparent to those skilled in the art and the invention is to be given its broadest possible interpertation within the terms of the following claims.

I claim:

1. A rotary scissor action cutting attachment for a hand held portion of a microsurgical instrument, said instrument including means in said hand held portion for producing rotary motion within said hand held portion with respect to the exterior of said instrument, said rotary scissor action cutting attachment comprising a) an elongated, axial, hollow tubular housing member, said housing member having a central axis and having a first end and a free end including a stationary blade and a movable blade, b) said tubular housing member including a hollow rotary bushing on the interior surface of said tubular housing member adjacent to said free end of said tubular housing member, said movable blade being rotatably supported within said hollow rotary bushing, c) support means for attaching said first end of said elongated tubular housing member to said hand held portion of said instrument, d) said stationary blade being attached to said hollow rotary bushing of said tubular housing member adjacent to said free end and having a stationary blade cutting surface extending at a transverse angle to said central axis of said tubular housing member, e) said movable blade including an elongated shaft portion and a movable blade cutting surface, said elongated shaft being rotatably supported within said hollow rotary bushing of said tubular housing member, said movable blade cutting surface extending at a transverse angle to said central axis of said tubular housing member at said free end of said tubular housing member, f) said extending transverse angle of said movable blade cutting surface being substantially similar to said extending transverse angle of said stationary blade cutting surface, said cutting surface of said stationary blade and said cutting surface of said movable blade facing each other and being adapted to contact each other in said scissor action with rotary movement of said movable blade with respect to said stationary blade, g) means in said support means for adjustably fixing said movable blade axially with respect to said tubular housing member to align axially said stationary blade cutting surface with said movable blade cutting surface, h) means in said support means for rotatably fixing said elongated shaft of said movable blade within said tubular housing member to align rotationally said movable blade cutting surface with respect to said stationary blade cutting surface to establish an open scissor alignment of said cutting surfaces, i) and means for engaging said rotary motion producing means within said hand held portion of said instrument with said means for rotatably fixing said elongated shaft of said movable blade within said tubular housing member adjacent to said first end, whereby rotary motion within said hand held portion of said instrument causes rotary scissor action between said cutting surface on said stationary blade and said cutting surface on said movable blade at said free end of said tubular housing member.

2. The rotary scissor action cutting attachment of claim 1 wherein said tubular housing member comprises an assembly of said hollow tubular member, said hollow rotary bushing and said hollow stationary blade member, said tubular member and said stationary blade member being attached to said bushing member with their hollow axes aligned to establish said central axis for said assembled tubular housing member.

3. The rotary scissor action cutting attachment of claim 1 wherein said hollow stationary blade member includes said stationary blade cutting surface at a transverse angle with respect to said axis of said assembled tubular housing member, said hollow stationary blade member being tapered from the exterior of said tubular member to an exterior tip spaced from said axis, and a sharpened edge on said stationary blade cutting surface at an angle to said stationary blade cutting surface from said exterior tip toward said axis.

4. The rotary scissor action cutting attachment of claim 3 wherein said transverse angle of said stationary blade cutting surface with respect to said axis of said tubular housing member is between about 0° and about 90°.

5. The rotary scissor action cutting attachment of claim 1 wherein said means for producing rotary motion of said movable blade includes a power operated means.

6. The rotary scissor action cutting attachment of claim 1 wherein said rotatably movable blade includes a portion extending at a transverse angle to said central axis, a cutting surface formed in said extending portion, said cutting surface having a cutting edge slanted with respect to a plane perpendicular to said central axis, said extending portion being resilient with respect to said cutting surface of said stationary blade cutting surface whereby said cutting surface of said stationary blade and said cutting surface of said rotable blade engage each other along moving contacting cutting surfaces as said movable blade is rotated with respect to said stationary blade.

7. The rotary scissor action cutting attachment of claim 1 wherein said means for producing rotary motion of said movable blade includes a manually operated means.

8. A stationary blade for a scissor action cutting attachment to a microsurgical instrument, said stationary blade comprising a) a tubular body portion with a radially extending blade portion, b) an axial tubular opening through said tubular body portion, c) a straight line cutting surface extending radially outwardly along said radially extending blade portion, said cutting surface being at a transverse angle from said axial tubular opening, d) one face of said cutting surface being a slanted face with respect to a plane perpendicular to said axial tubular body portion and extending from said tubular opening to the outward extended end of said cutting surface, e) and a sharpened edge at the edge of said slanted face of said cutting surface, said sharpened edge extending at an angle to said one face and from said tubular body portion to said outward extending end of said cutting surface.

* * * * *